United States Patent [19]

Cale, Jr. et al.

[11] Patent Number: 5,106,857

[45] Date of Patent: Apr. 21, 1992

[54] N-(1-METHYL-3-PYRROLIDINYL)-1-(PHENYLMETHYL)-1H-BENZIMIDAZOL-2-AMINE AND ANALOGS AS ANTIARRHYTHMIC AND MUSCLE RELAXING AGENTS

[75] Inventors: Albert D. Cale, Jr., Mechanicsville; Thomas W. Gero, Richmond, both of Va.

[73] Assignee: A. H. Robins Company, Incorporated, Richmond, Va.

[21] Appl. No.: 697,820

[22] Filed: May 9, 1991

[51] Int. Cl.$^5$ .................. A61K 31/445; A61K 31/415
[52] U.S. Cl. .................................... 514/322; 514/388
[58] Field of Search ................... 514/322, 387, 388

[56] References Cited

U.S. PATENT DOCUMENTS 4,219,559 8/1980 Janssens ........................ 424/267

OTHER PUBLICATIONS

J. Med. Chem. 28, 1925-33, 1934-43 (1985).

*Primary Examiner*—Frederick E. Waddell
*Assistant Examiner*—Kimberly R. Jordan
*Attorney, Agent, or Firm*—Robert F. Boswell, Jr.

[57] ABSTRACT

A method of treating cardiac arrhythmias and muscle tension and spasticity with N-(1-methyl-3-pyrrolidinyl)-1-(phenylmethyl)-1H-benzimidazol-2-amine and analogs and the pharmaceutical compositions are herein disclosed. Illustratively, the compound having the structure:

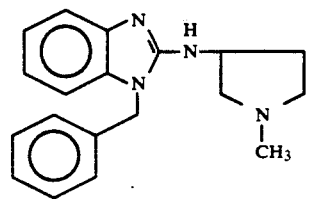

corrects an induced arrhythmia in 7 out of 8 dogs at 7 mg/kg IV and has an $ED_{50}$ of 21 mg/kg in the mouse Straub-tail test.

10 Claims, No Drawings

N-(1-METHYL-3-PYRROLIDINYL)-1-(PHENYL-METHYL)-1H-BENZIMIDAZOL-2-AMINE AND ANALOGS AS ANTIARRHYTHMIC AND MUSCLE RELAXING AGENTS

BACKGROUND OF THE INVENTION

1. Field of Invention

This invention relates to the use of N-(1-methyl-3-pyrrolidinyl)-1-(phenylmethyl)-1H-benzimidazol-2-amine and analogs thereof as antiarrhythmic agents as determined in the coronary occlusion model in dogs and muscle relaxants as determined by the Straub-tail in mice test.

The compounds useful in the method and composition of this invention are structurally related to the compounds of Formula A which

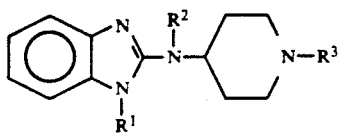

Formula A have been disclosed to have antihistaminic and antiallergic properties.

The Formula A compounds are disclosed in J. Med. Chem. 28(12), 1925–33 and 1934–43 (1985) and in U.S. Pat. No. 4,219,559. Compounds of Formula B where n is 0 or 2

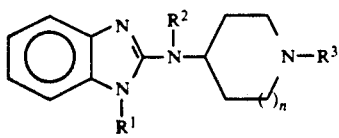

Formula B (i.e. pyrrolidine or homopiperidine) are disclosed in the European patent applications 282133 and 297661 as also having antihistaminic and antiallergy activities. Antiarrhythmic and muscle relaxant properties of the Formula A and B compounds have not been previously disclosed.

SUMMARY OF THE INVENTION

The antiarrhythmic and muscle relaxing compounds of this invention are encompassed by Formula I below:

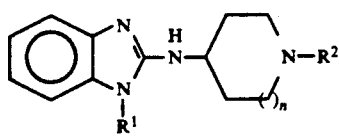

Formula I

Under Formula I, the groups $R^1$, $R^2$, and n are defined as follows:

n is 0 or 1,
$R^1$ is selected from H, $C_1$–$C_6$ alkyl, and benzyl; and
$R^2$ is $C_1$–$C_6$ alkyl.

Formula I also encompasses the pharmaceutically acceptable salts which includes solvates, hydrates, and acid addition salts. The acid addition salts are those salts formed from a Formula I compound and a non-toxic inorganic or organic acid such as hydrochloric acid, hydrobromic acid, sulfuric acid, citric acid, tartaric acid, hexamic acid, methanesulfonic acid, and the like.

Cardiac arrhythmias in dogs are induced by surgically restricting blood flow in a coronary artery. The test compound is administered intravenously and the heart rate and number and percentage of ectopic beats recorded at 15 minute intervals. A compound is considered active if it abolishes the ectopic beat and causes the heart to return to normal sinus rhythm within two hours of administration and partially active if it reduces but does not completely abolish the ectopic beats.

Administration of morphine sulfate to a mouse causes the tail to become elevated perpendicular to the body. Prior administration of a muscle relaxant compound inhibits this reaction known as the Straub tail.

DETAILED DESCRIPTION OF THE INVENTION

In contrast to the cyclodesulfurization method used in the preparation of the above Formula A and B compounds, the compounds useful in this invention are prepared from 1-(substituted or unsubstituted)-2-chlorobenzimidazole and 1-substituted-3-aminopyrrolidine by heating the reactants together with or without a solvent ($C_2$–$C_4$ alkanol) until the reaction ceases. The products are isolated and purified using standard extraction, crystallization, chromatographic, or salt preparation techniques.

The 1-(un)substituted-2-chlorobenzimidazoles are prepared by heating together a 2-hydroxybenzimidazole and excess phosphorus oxychloride while bubbling anhydrous hydrogen chloride gas into the mixture. A 1-substituted 2-chlorobenzimidazole can also be prepared by alkylating 2-chlorobenzimidazole.

For illustrative purposes, preparative procedures for the Formula I compounds and intermediates thereto are given below in the following Examples. These procedures are not limiting to this disclosure in any way. The chemicals used in these procedures are either commercially available or readily prepared by procedures appearing in the chemical and patent literature.

EXAMPLE 1

1-Ethyl-N-(1-ethyl-3-pyrrolidinyl)-1H-benzimidazol-2-amine

A. 2-Chlorobenzimidazole

A mixture of 2-hydroxybenzimidazole (300 g, 2.42 mol) and phosphorus oxychloride (1000 g) was heated at reflux temperature for 1 h to obtain a solution. Gaseous HCl was bubbled into the refluxing solution for 4 h and the solution then concentrated on a rotary evaporator. The residue was added to a mixture of aqueous potassium carbonate and methylene chloride and stirred for 18 h. The resulting mixture consisted of 2 liquid layers and a solid. The solid was collected and recrystallized from ethyl acetate and methanol.

B. Title compound

A solution of 11.4 g (0.1 mol) of 3-amino-1-ethylpyrrolidine and 14.4 g (0.08 mol) of 2-chloro-1-ethylbenzimidazole in 40 mL of ethanol was heated at reflux for 72 h. A mass spectal analysis showed the reaction to be about 25% complete. The solution was concentrated on the rotary evaporator (60° C./30 mm) and the residue was dissolved in 50 mL of n-butanol. The solution was heated to reflux for 24 h and partitioned between CHCl$_3$ and dilute NaOH. The CHCl$_3$ solution was dried (Na$_2$SO$_4$) and concentrated. The residue was chromatographed on the Waters Associates preparative HPLC (silica gel/isopropyl alcohol). The purified material was isolated as the fumarate salt by the following procedure.

The collected material (6 g, 0.023 mol) was treated with 2.7 g, 0.023 mol) of fumaric acid. The resulting crystals weighed 3.5 g and melted at 189°-191° C.

Analysis: Calculated for $C_{15}H_{22}N_4 \cdot 2C_4H_4O_4$: C, 56.32; H, 6.16; N, 11.42. Found: C, 56.22; H, 6.24; N, 11.48.

EXAMPLE 2

1-Ethyl-N-(1-methyl-3-pyrrolidinyl)-1H-benzimidazol-2-amine

A. 2-chloro-1-ethylbenzimidazole

1-Ethyl-2-benzimidazolinone (100 g, 0.62 mol) was dissolved in phosphorus oxychloride (475 mL) with stirring and heated to reflux temperature. Hydrogen chloride gas was passed into the refluxing solution for 4 h. Excess phosphorous oxychloride was removed on a rotary evaporator at 70° C. The residue was poured into a stirred mixture of aqueous potassium carbonate solution and methylene chloride. The mixture was basified with 50% sodium hydroxide solution and the methylene chloride layer was separated, dried ($Na_2SO_4$), concentrated, and distilled to obtain 86 g (77%) of oil, bp 110°-115° C./2-0.3 mmHg, which crystallized on standing; mp 50°-52° C.

B. Title compound

A solution of 38.6 g (0.21 mol) of 2-chloro-1-ethylbenzimidazole and 24 g (0.24 mol) of 3-amino-1-methyl-pyrrolidine in 150 mL of n-butanol was heated to reflux for 72 h and concentrated on the rotary evaporator (70° C./30 mm). The residue was partitioned between $CHCl_3$ and dilute NaOH. The $CHCl_3$ solution was dried ($Na_2SO_4$) and concentrated. For purification the material obtained was converted to the difumarate salt. The residue (68 g) was treated with a boiling solution of 64 g of fumaric acid in 600 mL of isopropyl alcohol and 100 mL of $H_2O$. The resulting salt weighted 48 g (63% yield). A sample was recrystallized from ethanol-$H_2O$, mp 204°-212° C. (dec).

Analysis: Calculated for $C_{14}H_{20}N_4 \cdot 2C_4H_4O_4$: C, 55.46; H, 5.92; N, 11.76. Found: C, 55.34; H, 5.93; N, 11.72.

EXAMPLE 3

N-(1-Methyl-3-pyrrolidinyl)-1-(phenylmethyl)-1H-benzimidazol-2-amine

A. 1-Benzyl-2-chlorobenzimidazole

A solution of 2-chlorobenzimidazole (100 g, 0.65 mol) in 500 ml of dimethylformamide (DMF) was added dropwise to a stirred suspension of 60% sodium hydride-mineral oil dispersion (28 g, 0.70 mol) in 500 ml of DMF. Mild intermittent cooling was required. After the addition was completed the mixture was stirred an additional 15 min and benzylbromide (82.6 g, 0.49 mol) was added dropwise with mild intermittent cooling. The reaction mixture was stirred an additional 1.5 h and 1 L of water was added. The mixture was extracted with benzene. The extract was dried ($Na_2SO_4$), concentrated and the residue crystallized from isopropyl ether to obtain 110 g (93%), mp 102°-105° C.

B. Title compound

To 14 g (0.14 mol) of 3-amino-N-methyl pyrroline was added 10.4 g (0.042 mol) of N-benzyl-2-chlorobenzimidazole and the reaction mixture heated to 125° C. for 2 days. The reaction mixture was partitioned between 150 mL of 1N NaOH and 100 mL of $CH_2Cl_2$. The aqueous layer was extracted again with 100 mL of $CH_2Cl_2$. The combined organic layers were washed with 100 mL of 1N NaOH, dried over $Na_2SO_4$, filtered, and concentrated by rotary evaporation and subjected to high vacuum at 100° C. for ~30 min. For purification, the residue was treated with 2 moles of oxalic acid in ethanol/2-propanol to afford 15 g (73%) of white analytically pure crystals, mp 211°-213° C. dec.

Analysis: Calculated for $C_{19}H_{22}N_4 \cdot 2C_2H_2O_4$: C, 56.79; H, 5.39; N, 11.52. Found: C, 56.40; H, 5.40; N, 11.40.

EXAMPLE 4

N-(1-Methyl-4-piperidinyl)-1-(phenylmethyl)-1H-benzimidazol-2-amine

A mixture of 18 g (0.157 mol) of 4-amino-1-methyl-piperidine and 7.5 g (0.0315 mol) of 2-chloro-1-(phenylmethyl)-1H-benzimidazole was heated to 130° C. for 24 hours (oil bath). Sodium hydroxide solution (150 ml, 2.5N) was added to the reaction mixture which was then extracted with $2 \times 200$ mL of $CH_2Cl_2$. The combined organic extracts were washed with 150 mL of $H_2O$, dried over $Na_2SO_4$, filtered and concentrated by rotary evaporation. The residue was subjected to high vacuum at 60° C. for two hours, and the resulting residue crystallized from acetone/$H_2O$. The resulting crystals were recrystallized from toluene and a trace of water to give 2.0 g (18%) of white analytically pure crystals as the dihydrate, mp 94°-102° C.

Analysis: Calculated for $C_{20}H_{24}N_4 \cdot 2H_2O$: C, 67.39; H, 7.92; N, 15.72. Found: C, 67.22; H, 7.85; N, 15.67.

CORONARY ARTERY LIGATION INDUCED ARRHYTHMIAS

Adult mongrel dogs which are in the conscious state were used for the test and cardiac arrhythmias were induced by prior (22-24 hr) surgical preparation in which blood flow through a coronary artery was occluded by use of a constrictor device as reported by Smith et al, 1973. A Grass Model 79 Polygraph was used for recording the electrocardiogram (Grass 7P4 Preamplifier).

The test compound was administered by infusion (Harvard Model 942 Infusion Pump) into a saphenous vein to the test group of dogs at a rate of 0.5 mg/kg/min. Concentration of compound was adjusted according to the weight of the dog to allow a volume of infusion of 0.5 ml/min. Following the administration of the test compound, the heart rate, number of ectopic beats (ectopic beats/HR $\times$ 1000) were recorded at 15 min intervals. The compound was considered active if it abolished the ectopic ventricular frequency and caused a return to normal sinus rhythm within 2 hours of administration. Cardiac arrhythmias produced by modification of method of Harris, 1950, Circulation 1, 1318, as reported by Smith et al, 1973, Pharmacologist 15, 192.

TABLE 1

| Compound | Antiarrhythmic Data Activity[1] | Dose(mg/kg IV) |
|---|---|---|
| 1 | ⅓ | 5 |
| 2 | partially active[2] | 7 |
| 3 | ⅓ | 7 |
| 4 | 2/6 | 9 |

[1]Number of dogs in which drug is considered active/number treated
[2]Reduces ectopic beats from 50-99%

MUSCLE RELAXANT TEST

The test procedure relied on to indicate positive muscle relaxant activity is the morphine-induced Straub Tail in Mice Test described by G. D. Novak in DRUG DEVELOPMENT RESEARCH (1982) 2: 383-386, except 8 animals per group were used per test rather than 10. The test is summarized as follows: The test drug, reference drug, and control articles to be administered are prepared in saline, 0.5% aqueous methylcellulose suspension or other, depending on solubility, in such concentration that the volume administered is 10 ml/kg. The initial screening dose of the test drug is usually 100 mg/kg. Groups of 8 mice are given an IP dose of a compound or vehicle prepared as described above. After 15 min, mice are administered morphine sulfate, 60 mg/kg in saline, subcutaneously. Fifteen minutes after administration of morphine (i.e., 30 min after test compound administration), mice were scored for presence of Straub Tail defined as an elevation of the tail at least 90 degrees from the horizontal. An $ED_{50}$ value may be determined from at least three logarithmically spaced doses by the method of Litchfield and Wilcoxon (1949), J. PHARMACOL. EXP. THER. 96: 99-113. The results obtained with the Formula I compounds are summarized in Table II below.

TABLE 2.

| | Muscle Relaxant Data | |
| --- | --- | --- |
| Compound | Straub Tail Inhibition %/Dose* | $ED_{50}$* |
| 1 | | 36 |
| 3 | | 21 |
| 4 | −25/100 | |

*dose or $ED_{50}$ mg/kg IP

PHAMACEUTICAL COMPOSITION AND ADMINISTRATION

Based on the results of the standard pharmacological test, these compounds are useful in the treatment of cardial arrhythmias and treating muscle tension and spasticity in warm-blooded animals. The compounds may be administered neat or with a pharmaceutical carrier to a warm-blooded animal in need thereof. The carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups and elixirs. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g., tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosages will be determined according to standard medical principles by a physician or veterinarian.

What is claimed is:

1. A method of treating cardiac arrhythmias which comprises administration to a warm-blooded animal in need thereof a therapeutically effective amount of a compound of the formula:

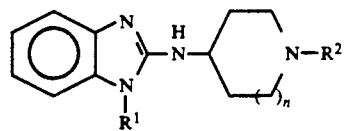

where
n is 0 or 1,
$R^1$ is selected from H, $C_1$-$C_6$ alkyl, and benzyl;
$R^2$ is $C_1$-$C_6$ alkyl,
or a pharmaceutically acceptable salt thereof.

2. A method of treatment according to claim 1 where the compound used is 1-ethyl-N-(1-ethyl-3-pyrrolidinyl)-1H-benzimidazol-2-amine or a pharmaceutically acceptable salt thereof.

3. A method of treatment according to claim 1 where the compound used is 1-ethyl-N-(1-methyl-3-pyrrolidinyl)-1H-benzimidazol-2-amine or a pharmaceutically acceptable salt thereof.

4. A method of treatment according to claim 1 where the compound used is N-(1-methyl-3-pyrrolidinyl)-1-(phenylmethyl)-1H-benzimidazol-2-amine or a pharmaceutically acceptable salt thereof.

5. A method of treatment according to claim 1 where the compound used is N-(1-methyl-4-piperidinyl)-1-(phenylmethyl)-1H-benzimidazol-2-amine or a pharmaceutically acceptable salt thereof.

6. A method of treating muscle tension and spasticity which comprises administration to a warm-blooded animal in need thereof a therapeutically effective amount of a compound of the formula:

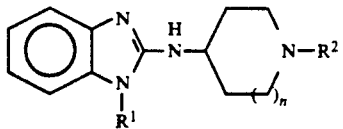

where
n is 0 or 1,
$R^1$ is selected from H, $C_1-C_6$ alkyl, and benzyl;
$R^2$ is $C_1-C_6$ alkyl, or a pharmaceutically acceptable salt thereof.

7. A method of treatment according to claim 6 where the compound used is 1-ethyl-N-(1-ethyl-3-pyrrolidinyl)-1H-benzimidazol-2-amine or a pharmaceutically acceptable salt thereof.

8. A method of treatment according to claim 6 where the compound used is 1-ethyl-N-(1-methyl-3-pyrrolidinyl)-1H-benzimidazol-2-amine or a pharmaceutically acceptable salt thereof.

9. A method of treatment according to claim 6 where the compound used is N-(1-methyl-3-pyrrolidinyl)-1-(phenylmethyl)-1H-benzimidazol-2-amine or a pharmaceutically acceptable salt thereof.

10. A method of treatment according to claim 6 where the compound used is N-(1-methyl-4-piperidinyl)-1-(phenylmethyl)-1H-benzimidazol-2-amine or a pharmaceutically acceptable salt thereof.

* * * * *